United States Patent [19]

Baron et al.

[11] Patent Number: 4,854,728

[45] Date of Patent: Aug. 8, 1989

[54] SEAWATER PROBE

[75] Inventors: George Baron, Rochester; William H. Vreeland, Scituate; Neil L. Brown, Woods Hole, all of Mass.

[73] Assignee: Sippican Ocean Systems, Inc., Marion, Mass.

[21] Appl. No.: 61,075

[22] Filed: May 18, 1987

[51] Int. Cl.$^4$ .................... G01D 3/02; G01K 13/00
[52] U.S. Cl. .................... 374/136; 73/170 A; 73/300; 374/1
[58] Field of Search .......... 374/142, 170, 1, 136; 73/170 A, 300; 324/63; 364/509

[56] References Cited

U.S. PATENT DOCUMENTS

| | | | |
|---|---|---|---|
| 2,750,794 | 6/1956 | Downs | 73/53 |
| 2,756,404 | 7/1956 | Anderson et al. | 340/347 AD |
| 3,147,431 | 9/1964 | Bennett et al. | 324/62 |
| 3,483,749 | 12/1969 | Francis | 374/136 |
| 3,675,484 | 7/1972 | Pederson | 331/66 |
| 3,748,899 | 7/1973 | Gregg et al. | 73/170 A |
| 3,991,623 | 11/1976 | Murdock | 73/170 A |
| 4,041,382 | 8/1977 | Washburn | 324/65 R |
| 4,122,719 | 10/1978 | Carlson et al. | 374/167 X |
| 4,324,138 | 4/1982 | Davis et al. | 374/167 X |
| 4,359,285 | 11/1982 | Washburn | 374/172 |
| 4,562,554 | 12/1985 | Stixrud et al. | 364/557 X |

Primary Examiner—Daniel M. Yasich

[57] ABSTRACT

A seawater probe for measuring a physical parameter which includes a sensor element having an electrical characteristic dependent on the parameter and a detector circuit for deriving a measurement signal corresponding to a measured value of the electrical characteristic, the improvement including a reference element having a known, stable value of the electrical characteristic connected in series with the sensor element, the reference and sensor elements being powered by a single power supply, means for selectively connecting the sensor and reference elements separately in the detector circuit, and means for calibrating the detector circuit using the known value of the electrical characteristic of the reference element and the measurement signal derived when the reference element is in the detector circuit.

10 Claims, 4 Drawing Sheets

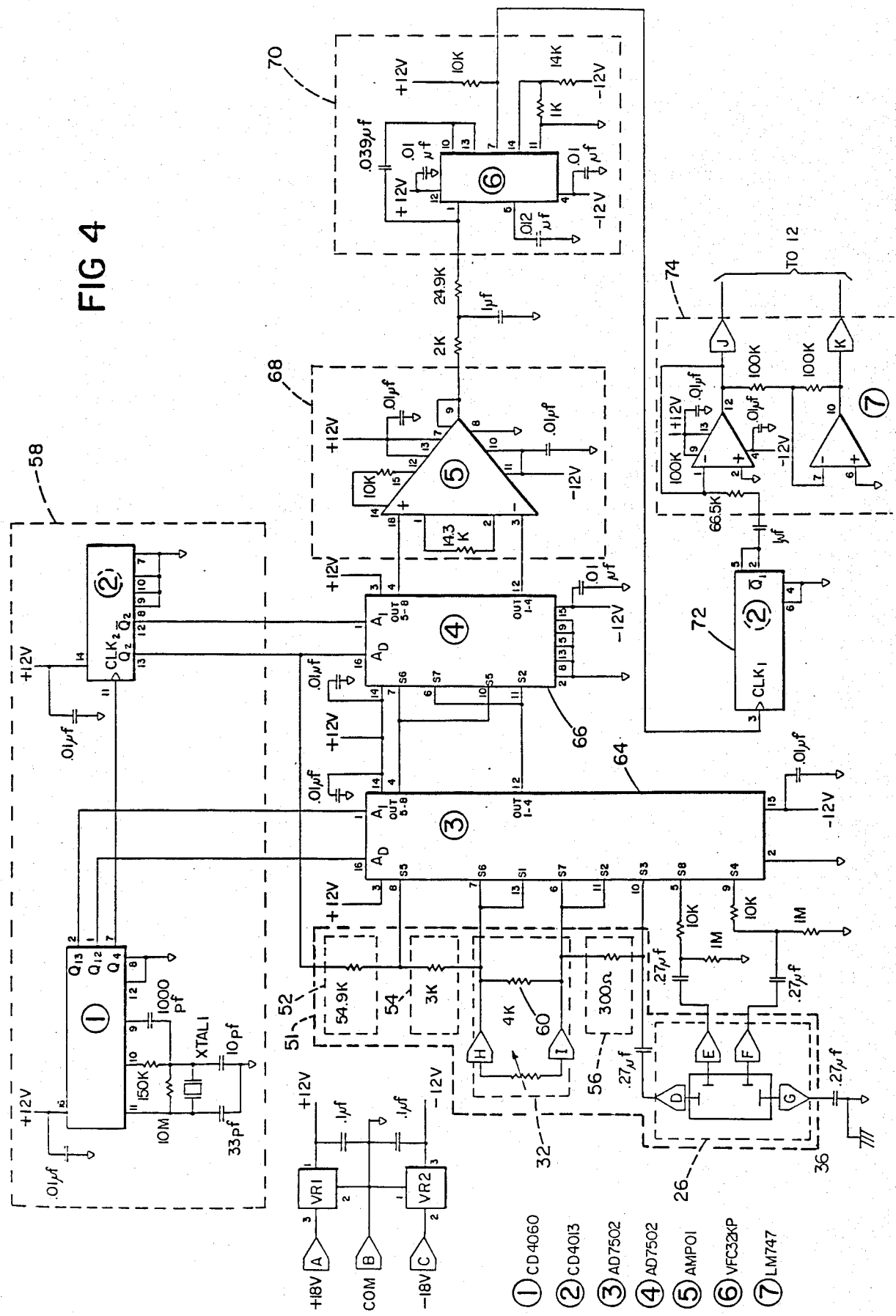

4,854,728

SEAWATER PROBE

This invention was made with Government support under Contract N00014-82-C-0579 awarded by the Department of the Navy. The Government has certain rights in the invention.

This is a continuation of co-pending application Ser. No. 613,918 filed on May 25, 1984 and now abandoned.

BACKGROUND OF THE INVENTION

This invention relates to probes for remotely measuring thermal and electrical characteristics of seawater.

Such probes generally consist of a deployable probe unit which includes sensors for measuring the target characteristics, e.g., conductivity cells and temperature sensors, means (e.g., wires) for transmitting signals generated by the sensors to a base station, and circuitry for translating the signals received from the sensors into data reflecting the characteristics being measured. Since it is usually desired to be able to reliably compare data generated by different probes, it is necessary to ensure that different probes will generate the same data under the same conditions. One way to achieve this is to manufacture the sensors to very exact dimensions and very low error tolerances. Another, less expensive, way is to provide means for accurately calibrating the signals generated by the sensors.

SUMMARY OF THE INVENTION

In general, the invention features in a seawater probe for measuring a physical parameter which includes a sensor element having an electrical characteristic dependent on the parameter and a detector circuit for deriving a measurement signal corresponding to a measured value of the electrical characteristic, an improvement including a reference element having a known, stable value of the electrical characteristic connected in series with the sensor element, the reference and sensor elements being powered by a single power supply, means for selectively connecting the sensor and reference elements separately in the detector circuit, and means for calibrating the detector circuit using the known value of the electrical characteristic of the reference element and the measurement signal derived when the reference element is in the detector circuit.

In preferred embodiments, the sensor element measures temperature and the probe includes an additional sensor element for measuring conductivity; the probe includes an additional reference element having a different known, stable value of the electrical characteristic from the reference element; the power supply is an AC source; the probe includes means for storing predetermined values of the electrical characteristics of the sensor elements, the values being measured at two or more known values of the parameters, and the detector means includes means for generating a curve-fitting equation using the predetermined values and means for inputting the measured sensor value to the equation to derive the measurement signal; and the connecting means further includes a multiplexer for repeatedly and alternately connecting the reference and sensor elements into the detector circuit so as to generate a successive plurality of calibrated measurements.

Since the probe uses extremely stable reference elements to calibrate each measurement, the actual sensor elements do not need to be accurate in the absolute sense but need only be stable. Also, since the resistors are all connected in series and powered from a common source, the source does not need to be extremely stable, since any variatiions will be reflected in the signals generated by each of the resistors and so will, in effect, be canceled out. The probe can thus be constructed from inexpensive parts, making the manufacture of an expendable seawater probe which generates accurate measurements of temperature and conductivity economically feasible. Further, by knowing the depth (and hence the pressure) at which the measurements are made, accurate salinity data can be calculated which can then be used in a wide range of ocean science studies.

Other features and advantages of the invention will be apparent from the following description of the preferred embodiment thereof, and from the claims.

DESCRIPTION OF THE PREFERRED EMBODIMENT

We first briefly describe the drawings.

Drawings

FIG. 4 is a detailed electrical schematic of the probe circuitry.

Structure

Figure 1:
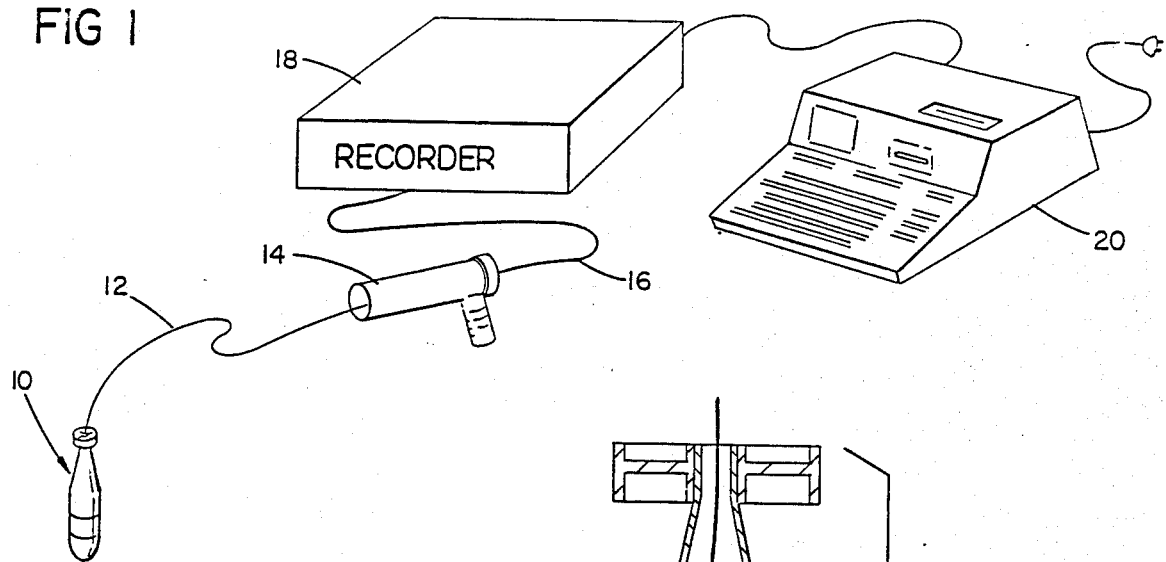
FIG. 1 is a diagrammatic view of the overall probe system configuration.

Referring to FIG. 1, the probe system includes deployable probe unit 10, connected by standard 39 gauge BT wire 12 to hand-held launcher 14. Alternatively, launcher 14 may be a deck or through-hull launcher. Launcher 14 is connected by launcher cable 16 to a Sippican Ocean Systems MK9 recorder 18, which filters and demultiplexes the time-multiplexed frequency-modulated data received from probe unit 10 and measures the frequencies of the data samples. Recorder 18 is connected via an IEEE-488 digital bus to desk top computer 20, e.g., a Hewlett Packard HP85, which corrects the data received for gain and offset of the electronics, displays and prints the corrected data, and stores the data on a magnetic tape cassette.

Figure 2:
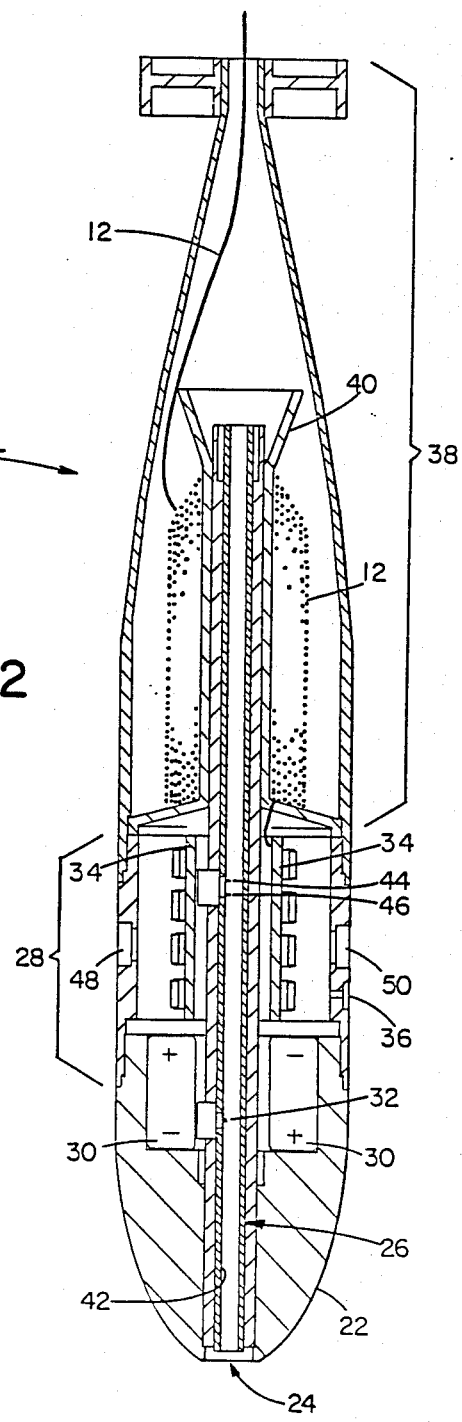
FIG. 2 is a diagrammatic cross-sectional view of the deployable probe.

Referring now to FIG. 2, at the front of deployable probe unit 10 in zinc nose 22 having center hole 24, which provides a controlled rate of stable descent while allowing water flow through conductivity cell 26. Forebody 28, immediately behind nose 22, houses power supply 30, thermistor 32, printed circuit (PC) boards 34, seawater activation electrodes 36, and much of conductivity cell 26. Afterbody 38, open at the rearward end, provides protection for the end of conductivity cell 26 and houses spool 40, around which wire 12 is wound. Power supply 30 and PC boards 34 are potted to ensure water integrity.

Thermistor 32 is a glass encapsulated thermistor with a tolerance specified at ±25% from the nominal resistance of 2K at 25° C., e.g., a Thermometrics type P50BA202M. Since calibration data obtained at the time of manufacture of the probe unit is used (as will be described) during actual measurements which may take place some time after manufacture, the thermistor should be extremely stable, i.e., exhibit low drift. For example, the thermistor has been shown to exhibit a drift of approximately 0.001° C. in two years. Typically, the thermistor must also have a fast response to temperature changes so as to accurately measure the temperature at the rate of descent through the water. The thermistor chosen will sense a 1° C. step change in temperature to within 0.01° C. in less than 100 ms.

Conductivity cell 26 is a Pyrex or quartz glass tube 42, approximately 8 inches in length with an internal diameter of 0.158 inches and an outer diameter of 0.24 inches. Tube 42 extends along the central axis of probe unit 10 from center hole 24 of nose 22 into afterbody 38 and has four platinum electrodes 44, 46, 48, 50 coated with highly porous platinum black. Inner electrodes 44, 46 extend into glass tube 42 and outer electrodes 48, 50 extend from forebody 28 to the exterior of the probe. Electrodes 44, 48 are current electrodes and electrodes 46, 50 are voltage electrodes. The porous platinum black coating, formed by electrolyzing an aqueous solution of 0.3% platinum chloride and 0.025% lead acetate into which the electrodes are placed, economically increases electrode surface area (and therefore electrode efficiency).

Thermistor 32 and electrodes 44, 46, 48, 50 are connected through PC boards 34 to wire 12, which is wound around spool 40 and which is connected to launcher 14 as shown in FIG. 1.

Power supply 30 consists of six alkaline 6 V batteries contained within the probe which provide a total of ±18 V; the voltage is regulated down to ±12 V. The batteries should retain a high percentage, e.g., 70%, of their original capacity after two years if stored at temperatures less than 30° C. At circuit current drains of approximately 30 ma the batteries are capable of powering the probe throughout its descent.

Activation of the probe electronics is achieved via the seawater activation electrodes 36 on the outside of the probe body. The electrodes are commoned to circuit ground, which is also seawater ground, upon contact with seawater, thus completing the power/ground circuit.

Figure 3:
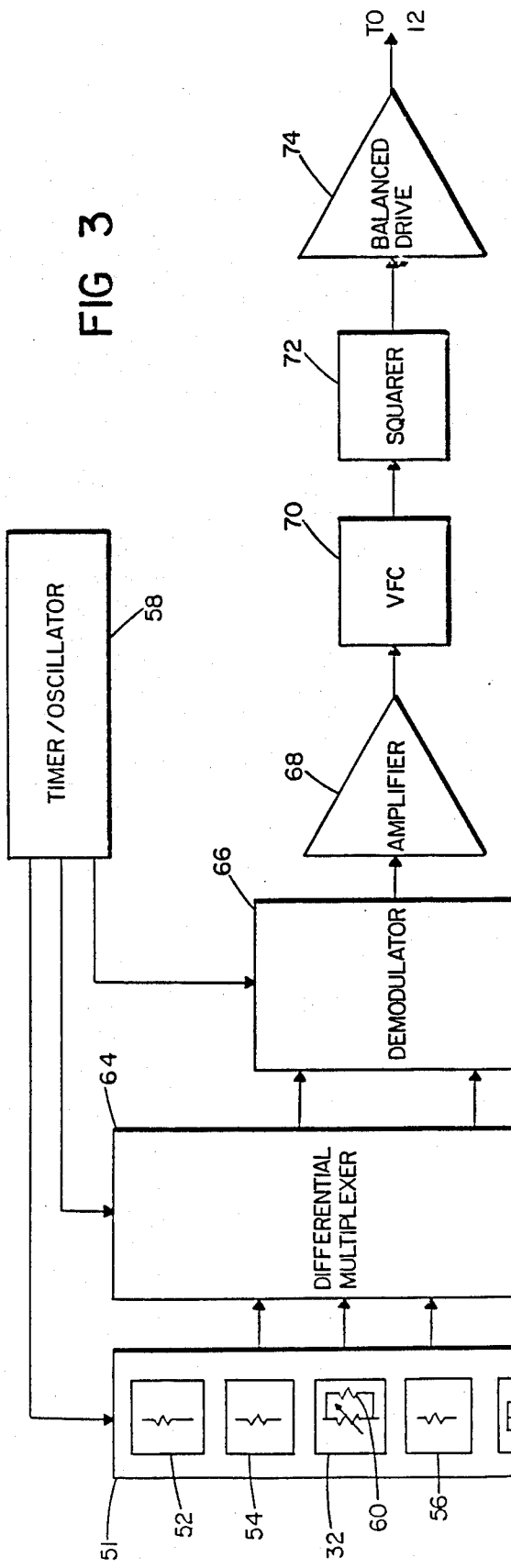
FIG. 3 is a functional block diagram of the electrical circuitry contained within the deployable probe unit.

FIG. 3 is a block diagram showing the relationship between the electronic components of deployable probe 10. Resistor chain 51 consists of resistor 52 ($R_S$), high calibration resistor 54 ($R_{HI}$), thermistor 32 ($R_T$) (which includes shunt resistor 60 ($R_{TS}$)), low calibration resistor 56 ($R_{LO}$), and conductivity cell 26 ($R_C$), all connected in series. $R_{TS}$ is connected across $R_T$ so as to reduce the current flowing through $R_T$ (and therefore the amount of power and heat dissipated by $R_T$) without affecting the current flowing through the remainder of resistor chain 51. ($R_{TS}$ has the same effect on all measurements of $R_T$ and so is automatically accounted for by the calibration procedure described below.) $R_{TS}$, $R_{HI}$, and $R_{LO}$ are Vishay Type S102 resistors; $R_{HI}$ and $R_{LO}$ each have a resistance tolerance of ±0.005% and a temperature coefficient of 1 part per million per °C., i.e., are extremely stable, and $R_{TS}$ has a tolerance of ±1% at the same stability. $R_S$ also has a tolerance of ±1%, and has a resistance of 54.9 kohms; $R_S$ serves to control the overall current flowing through the subsequent resistors in the chain. $R_{HI}$, whose resistance is 3 kohm, and $R_{LO}$, whose resistance is 300 ohm, are used as calibration standards for $R_T$ and $R_C$.

Resistor chain 51 is connected in series with timer/oscillator 58. Timer/oscillator 58 outputs a positive square wave signal which drives resistor chain 51. $R_{HI}$, $R_T$, $R_{LO}$, and $R_C$ (54, 32, 56, and 26, respectively) output four separate AC voltage signals in response to the input square wave signal. Since the same current flows through all of the resistors, and since the sampling rate is so fast, it is not necessary to have an extremely stable current source; any variations in the current flowing will be equally reflected by all of the resistors and so will be accounted for by the calibration process (discussed below).

Timer/oscillator 58 also drives 4-channel differential multiplexer 64, which thus provides the channel address signals. Multiplexer 64 sequentially addresses each of the four data channels, corresponding to $R_{LO}$, $R_C$, $R_{HI}$, and $R_T$, for approximately 60 ms each, resulting in sampling rate of better than 4 Hz, to collect the output voltage signals.

The time-multiplexed output from multiplexer 64 is sent to synchronous demodulator 66, which is also driven by timer/oscillator 58. Demodulator 66 converts the time-multiplexed AC signal from multiplexer 64 to a DC signal and transmits the DC signal to instrumentation amplifier 68. The amplifier time-multiplexed DC signal is sent to Voltage-to-Frequency Converter (VFC) 70, which converts the signal to a proportional time-multiplexed frequency. This signal is divided by two by squarer 72 to generate a 50% duty cycle square wave, and fed to balanced driver 74 for transmission to the MK9 recorder 18, shown in FIG. 1.

FIG. 4 shows a detailed electrical schematic, including integrated circuit (IC) components and circuit values, of the circuit just described. IC1 of timer/oscillator 58 is a multivibrator which outputs three 1 kHz AC signals, $Q_4$, $Q_{12}$, and $Q_{13}$. The $Q_4$ output is divided down by IC2, which outputs $Q_2$ and $\overline{Q}_2$. $Q_2$ drives resistor chain 51; $R_{LO}$, $R_C$, $R_{HI}$, and $R_T$ output four separate voltages to differential multiplexer 64 (IC3) in response to the applied square wave signal.

Differential multiplexer 64 is driven by the $Q_{12}$ and $Q_{13}$ outputs of oscillator 58, providing the multiplexer sampling rate of 60 ms across each of $R_{LO}$, $R_C$, $R_{HI}$, and $R_T$.

Both the $Q_2$ and $\overline{Q}_2$ outputs of IC2 are also the driving signal for the synchronous demodulator 66 (IC4). Demodulator 66 receives the time-multiplexed AC voltage signal from multiplexer 64 and converts it rapidly to a DC signal. The DC signal is amplified by IC5 of instrumentation amplifier 68 and input to IC6 of VFC 70.

VFC 70 outputs a time-multiplexed frequency proportional to the input DC voltage in the range of approximately 400 to 2600 Hz. Squarer 72, also on IC2, divides the output of VFC 70 by two to achieve the desired 50% duty cycle square wave. The resulting 200–1300 Hz square wave signal is then AC coupled to balanced driver 74 (IC7) which compensates for the high wire attenuation by providing a very large voltage swing. When IC7, pin 12 is positive at about 6 V, IC7, pin 10 is negative at −6 V. Therefore, IC7, pin 12, swings from 6 V to −6 V, while IC7, pin 10, simultaneously swings from −6 V to 6 V, creating a total voltage swing of 24 V. The resulting time multiplexed frequency signal is then transferred to the MK9 recorder 18 at the surface, shown in FIG. 1.

Operation

In advance of use, preferably at the time of manufacture, the probe is characterized by measuring its response to known conditions of temperature and conductivity and the characterizing data is stored for later use in actual measurements, as explained below. When a measurement is to be made, the probe unit is launched into the water using a hand, deck, or through-hull launcher. The probe electronics are activated when the seawater activation electrodes 36 come into contact with seawater as previously described; sampling at a probe sampling increments of 1 meter begins immediately. Data in the form of measured frequencies across $R_{HI}$, $R_T$, $R_{LO}$, and $R_C$ is transmitted to the surface MK9 Recorder and is operated on by the surface computer, as explained below, to generate the measured values of temperature and conductivity. The computer also generates corresponding depth data by knowing the elapsed time of fall for the probe and the fall rate, which is assumed to be 12.78 ft/sec in the "average" ocean.

Characterization data for each probe is required since each thermistor and conductivity cell may respond differently to the same temperature and conductivity, respectively. However, since each thermistor (or conductivity cell) is extremely stable over time, the response of a given thermistor (or conductivity cell) to a given temperature (or conductivity) will remain constant for the life of the probe, i.e., from the time of manufacture through the actual use of the probe, even if the probe is stored for as long as two years between manufacture and use. The characterization data obtained at the time of manufacture is thus valid for the life of the probe and is stored with the probe so as to be available at the time of the probe's use.

Figure 5:
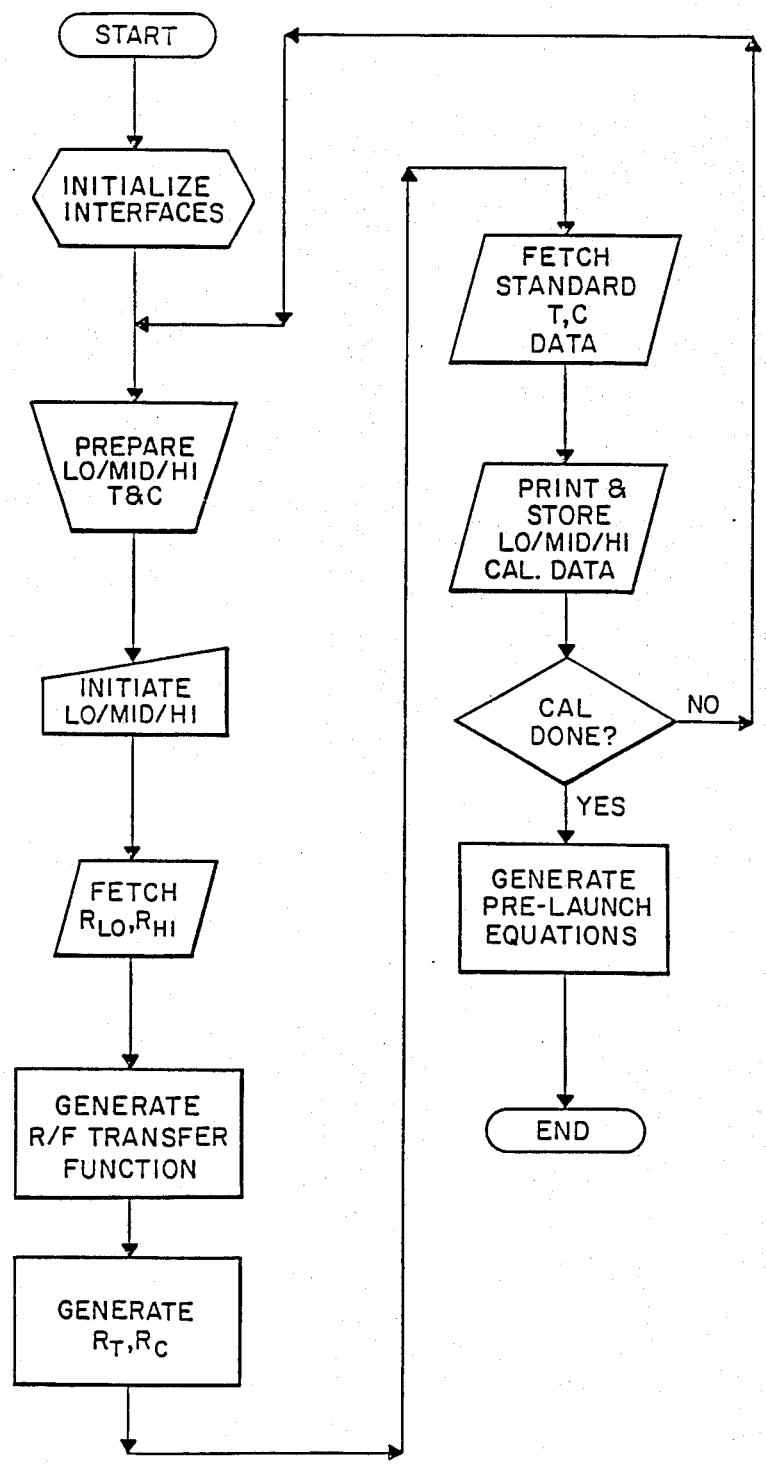
FIG. 5 is a flow chart of the probe calibration procedure.

The characterization data of a probe, i.e., the response of the probe's thermistor and conductivity cell to known temperatures and conductivities, respectively, is generated at three known values (a low, middle, and high value) of temperature and conductivity within the probe's operating range. A flow chart of the calibration procedure is shown in FIG. 5. Instrument interfaces are first initialized as required, e.g., by the HP85. Following the instrument initialization the operating program (in the HP85) requests a low, middle, or high calibration run and the probe to be characterized is immersed in the low/middle/high bath along with a standard probe, e.g., a Neil Brown Instruments Conductivity/Temperature Standard.

Following immersion of the probes in the bath, the computer fetches the frequencies generated by the probe's $R_{HI}$ and $R_{LO}$ standard resistors. Using these values the computer generates a circuit transfer function having the form:

$$R = \frac{R_{HI} - R_{LO}}{F_{RHI} - F_{RLO}} (F - F_{RHI}) + R_{HI}$$

wherein $R_{HI}$ is the kniown resistance of standard resistor $R_{HI}$ (3 Kohm±0.005%) and $F_{RHI}$ is its resulting output frequency (measured), and $R_{LO}$ is the known resistance of the standard resistor $R_{LO}$ (300 ohms±0.005%) and $F_{RLO}$ is its resulting output frequency (measured). The resistance R of the thermistor $R_T$ (or conductivity cell $R_C$) at the temperature (or conductivity) of the bath can then be calculated using the circuit transfer function for that bath and the measured frequency F of $R_T$ (or $R_C$). The actual temperature and conductivity of the bath is determined by the standard probe. Thus for each bath (calibration run), the following data is generated:

$T_{HI}$, $R_{THI}$ . . .

Actual temperature of the high calibration bath and the calculated resistance of the thermistor $R_T$ $T_M$, $R_{TM}$ . . .
Middle calibration bath $T_L$, $R_{TLO}$ . . .
Low calibration bath $C_{HI}$, $R_{CHI}$ . . .
Actual conductivity of the high calibration bath and the calculated resistance of the conductivity cell $R_C$ $C_M$, $R_{CM}$ . . .
Middle calibration bath $C_{LO}$, $R_{CLO}$ . . .
Low calibration bath The calibration data can be stored on cassette tape for later use during actual measurements; the tape would be packaged one per each case of 12 probes. The tape would contain not only the calibration data but would also provide the storage medium for the measured data.

Figure 6:
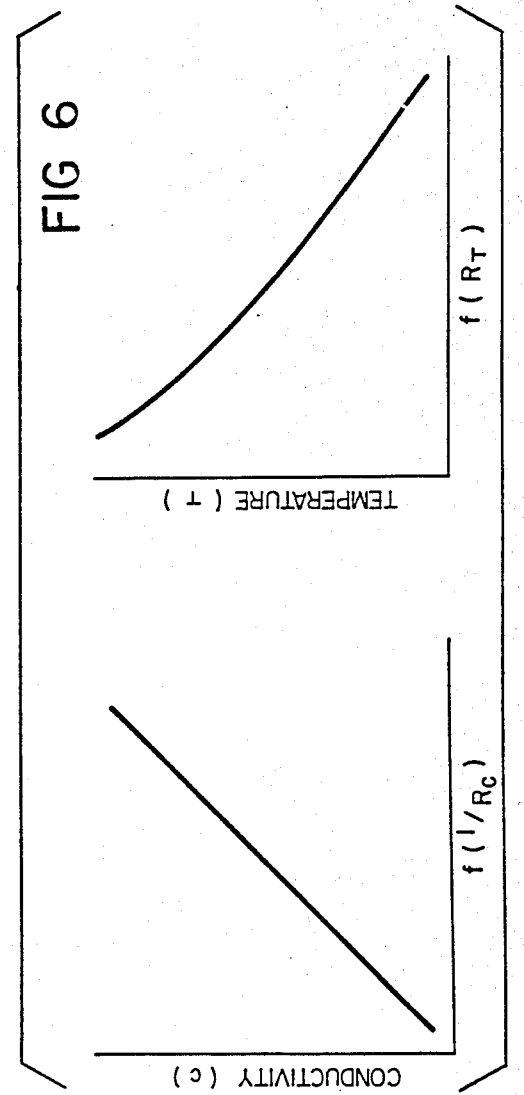
FIG. 6 is a generalized graph of the pre-launch equations generated for each probe.

Using the calibration data, prelaunch equations are generated for $R_T$ and $R_C$. The pre-launch equations, which are shown graphically in FIG. 6, are curve-fitting equations which use the probe characterizing data to generate functions of temperature and conductivity in terms of resistance. These equations are fixed for the life of the probe; therefore after the generation of the equations the probe is ready for actual use.

In actual use, the probe is deployed as previously described and begins transmitting data to the surface MK9 Recorder. Each sequence of four frequency values, i.e., $F_{RHI}$, $F_{RT}$, $F_{RLO}$, and $F_{RC}$, is one measurement cycle. For each measurement cycle, the computer fetches the $F_{RHI}$ and $F_{RLO}$ values from the recorder and generates a circuit transfer function just as described for the calibration runs. This recalibration for each cycle compensates for any circuit variations such as amplifier gain, offset, drift, power supply variations, and the like. Using the circuit transfer function and the measured $F_{RT}$ and $F_{RC}$ values, the resistance values of $R_T$ and $R_C$, respectively, are calculated. These are then input to the previously determined pre-launch equations to determine the actual temperature and conductivity, respectively, of the water being tested. The final measured values of temperature and conductivity are printed out with corresponding depth data and can be stored for later use.

Other embodiments are within the following claims. For example, to store the characterizing data a bar code could be used which would be printed on the outside of each probe, with an "intelligent" launcher or launcher modification kit being provided to automatically read the data prior to launch; the data could be stored on an expendable PROM or magnetic card supplied with each case of probes which could be implemented in the MK9 processor; or calibration data supplied with each probe could be entered via the HP85 keyboard by the operator just prior to launching of the probe.

What is claimed is:

1. Apparatus for measuring conductivity and temperature of seawater, said apparatus comprising
   a seawater probe comprising
      a housing,
      a conductivity cell mounted on said housing so as to be exposed to seawater,
      a thermistor or other means for measuring temperature, mounted on said housing so as to be exposed to seawater, one or more stable reference resistors, power supply means for supplying an AC current to said conductivity cell, thermistor, and reference resistors, multiplexer means for alternately sampling the AC voltage across said conductivity cell, thermistor, and reference resistors, circuit means for converting the multiplexed AC voltage output of said multiplexer means into an output signal for transmission across said wire, means for storing on or in said probe unique characterization data for said probe in a manner accessible from outside said probe prior to launch thereof, said characterization data comprising data points relating actual conductivity to voltage at said conductivity cell and actual temperature to voltage at said thermistor, and circuitry external to said probe (e.g., onboard ship) for receiving and analyzing said output signal, said circuitry comprising means for receiving said characterization data prior to launch of said probe means for processing said output signal to determine said voltages sampled across said conductivity cell and thermistor, by comparing output signals corresponding to samples taken at said conductivity cell and thermistor to output signals for samples taken across said reference resistors, means for using said characterization data to convert said voltage measurements to actual conductivity and temperature measurements.

2. The apparatus of claim 1 further comprising a spool of wire on said housing and means for paying out said wire as said probe descends, and means for providing descent times from which the depth of said conductivity and temperature measurements can be inferred using an estimated descent rate for the probe.

3. The apparatus of claim 1 wherein said characterization data comprises for each measured parameter (conductivity or temperature) at least three data points, each point representing the value of said parameter at a known value of voltage for the corresponding sensor (conductivity cell or thermistor).

4. The apparatus of claim 1 wherein said output signal is frequency modulated (FM) so that the frequency of said signal is proportional to the voltages sampled at said conductivity cell, thermistor, and reference resistors.

5. The apparatus of claim 1 wherein said reference resistors are connected in series with said conductivity cell and thermistor.

6. The method of measuring seawater conductivity and temperature comprising the steps of providing a seawater probe having a conductivity cell and thermistor exposed to seawater, providing one or more stable reference resistors in said probe, providing an AC current to said conductivity cell, thermistor, and reference resistors, alternately sampling the AC voltage across said conductivity cell, thermistor, and reference resistors, converting the sampled AC voltage into an output signal for transmission across said wire, generating in advance of use of said probe a set of unique characterization data for said probe, said characterization data comprising data points relating actual conductivity to voltage across said conductivity cell and actual temperature to voltage across said thermistor, reading said characterization data from said probe prior to launch thereof, determining the voltages of said sensors (conductivity cell and thermistor) from the signal received from said probe by comparing output signals for samples taken at said sensors to signals for samples taken at said reference resistors, using said characterization data to convert said voltage measurements to actual conductivity and temperature measurements by fitting a curve through said characterization data for a particular parameter (conductivity or temperature) and looking up said actual parameter on said curve using said voltage measurement.

7. The method of claim 6 comprising the further step of providing corresponding depth data by inferring depth from descent time using an estimated descent rate for said probe.

8. The method of claim 6 wherein characterization data comprises for each measured parameter (conductivity or temperature) at least three data points, each point representing the value of said parameter at a known value of voltage for the corresponding sensor (conductivity cell or thermistor).

9. The method of claim 6 wherein the output signal of said probe is frequency modulated (FM) so that the frequency of said signal is proportional to the voltages sampled at said conductivity cell, thermistor, and reference resistors.

10. The method of claim 6 wherein said reference resistors are connected in series with said conductivity cell and thermistor.

* * * * *